US012594336B2

(12) United States Patent
Smith

(10) Patent No.: US 12,594,336 B2
(45) Date of Patent: Apr. 7, 2026

(54) TRACE ELEMENT SOLUTION

(71) Applicant: WARBURTON TECHNOLOGY LIMITED, Dublin (IE)

(72) Inventor: William Alfred Smith, Dublin (IE)

(73) Assignee: Warburton Technology Limited, Dublin (IE)

( * ) Notice: Subject to any disclaimer, the term of this patent is extended or adjusted under 35 U.S.C. 154(b) by 287 days.

(21) Appl. No.: 17/355,791

(22) Filed: Jun. 23, 2021

(65) Prior Publication Data

US 2021/0315997 A1     Oct. 14, 2021

Related U.S. Application Data

(63) Continuation of application No. 14/400,902, filed as application No. PCT/IB2012/052389 on May 14, 2012, now abandoned.

(51) Int. Cl.

| | |
|---|---|
| A61K 33/32 | (2006.01) |
| A23K 20/174 | (2016.01) |
| A23K 20/20 | (2016.01) |
| A23K 50/10 | (2016.01) |
| A61K 9/00 | (2006.01) |
| A61K 31/714 | (2006.01) |
| A61K 33/04 | (2006.01) |
| A61K 33/18 | (2006.01) |
| A61K 33/24 | (2019.01) |
| A61K 33/30 | (2006.01) |
| A61K 33/34 | (2006.01) |
| A61K 47/24 | (2006.01) |

(52) U.S. Cl.
CPC ............ *A61K 47/24* (2013.01); *A23K 20/174* (2016.05); *A23K 20/30* (2016.05); *A23K 50/10* (2016.05); *A61K 9/0019* (2013.01); *A61K 31/714* (2013.01); *A61K 33/04* (2013.01); *A61K 33/18* (2013.01); *A61K 33/24* (2013.01); *A61K 33/30* (2013.01); *A61K 33/32* (2013.01); *A61K 33/34* (2013.01)

(58) Field of Classification Search
None
See application file for complete search history.

(56) References Cited

U.S. PATENT DOCUMENTS

| | | | | |
|---|---|---|---|---|
| 4,335,116 A | * | 6/1982 | Howard | A61K 31/315 514/505 |
| 2004/0132689 A1 | * | 7/2004 | Nishida | A61K 33/30 536/54 |
| 2005/0244511 A1 | * | 11/2005 | Laurie | A61K 33/32 424/641 |
| 2011/0065665 A1 | * | 3/2011 | Heep | A61P 43/00 514/52 |
| 2011/0076341 A1 | * | 3/2011 | Smith | A61K 33/24 424/630 |

FOREIGN PATENT DOCUMENTS

| | | | | |
|---|---|---|---|---|
| WO | WO-0217933 A1 | * | 3/2002 | A61K 45/06 |

OTHER PUBLICATIONS

Trace Element Supplementation. https://meatpromotion.wales/images/resources/HCC_Trace_elements_A5_low_res.pdf. Published: Apr. 2011.*
Addamel N. https://www.fresenius-kabi.com/cl/documents/SmPC_Addamel_N.pdf. Published: Jun. 18, 2010.*
Bayer. https://www.pig333.com/company_news/bayer-animal-health-introduces-catosal%E2%84%A2-10-butaphosphan-cyanocobala_591/. Published: Feb. 13, 2009.*

* cited by examiner

*Primary Examiner* — Nicole P Babson
*Assistant Examiner* — Lori K Mattison
(74) *Attorney, Agent, or Firm* — Covington & Burling LLP; Einar Stole

(57) ABSTRACT

A trace element solution comprises at least the following metals: zinc; manganese; selenium; and copper; and which comprises Vitamin B12. The solution furthermore comprises butaphosphan to stabilize the Vitamin B12 and the inclusion of butaphosphan may have synergistic activity with the minerals.

12 Claims, 2 Drawing Sheets

TRACE ELEMENT SOLUTION

CROSS REFERENCE TO RELATED APPLICATION

This is a continuation of U.S. application Ser. No. 14/400,902, a 371 national stage of PCT/IB2012/052389, filed May 14, 2012, all herein incorporated by reference.

FIELD OF INVENTION

The present invention relates to a trace element solution. More particularly, the present invention relates to a trace element solution supplemented with Vitamin B12.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that the concentrations of the minerals in the solutions is too low. This means that relatively large quantities have to be injected, which in turn causes tissue damage and also abscesses at the site of injection. Furthermore, it is generally the case that different trace elements seldomly are individually sufficient. This means that two or more trace element solutions have to be provided by way of separate injections.

ZA 1982/6778 (Laurie) discloses a trace element solution and a method of providing the trace elements to livestock. These trace element solutions include ethylene diamino tetra acetic acid complex of the required mineral in suitable quantities. However, the trace element solution includes no selenium or selenite compound.

In the specification and claims the expression EDTA refers to ethylene diaminotetraacetic acid ($C_{10}H_{16}O_8N_2$ or $(HO_2CH_2C)_2NCH_2CH_2N-(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem arises when mixtures of high concentration are needed. In certain cases it would be impossible to deliver them, because mixing is always accompanied by dilution. The maximum concentration achieved with this method was 13.5 mg/ml.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

U.S. Pat. No. 7,285,292 (Laurie et al) discloses a trace element solution, which comprises at least one metal selected from the group comprising selenium, copper, zinc, manganese and chromium and which comprises a concentration of the metal(s) of at least 60 mg/ml. The solution further comprises at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide. The trace element solution is prepared by a method consisting essentially of the steps of preparing a $MnCO_3$ mixture in a container; adding an EDTA/NaOH mixture to the container and subsequently adding at least one metal compound; and adding $Na_2SeO_3$ to the container to obtain the trace element solution. The method also comprises the step of adding $CrCl_3.6H_2O$ to the trace element solution.

Often various other nutritional, dietary or medical components need to be added to the trace element solutions. Though which seems easy to achieve by merely mixing has not proven to be easy as the resulted mixture or solution becomes unstable and murky over time and hence the solution needs to be discarded. The disadvantage is that the solutions cannot be stored for longer periods. Addition of further components is more difficult than it appears resulting in both physical solution instability and in some cases such as vitamin B12 addition-chemical instability.

It is an object of the invention to suggest a trace element solution for overcoming these problems.

SUMMARY OF INVENTION

According to the invention, a trace element solution, comprises at least the following metals:
(a) zinc;
(b) manganese;
(c) selenium; and
(d) copper;
and comprises Vitamin B12.

The ratio of zinc to manganese may be at least 2:1.
The ratio of zinc to manganese may be at least 4:1.
The ratio of zinc to copper may be at least 2:1 or 4:1.
The ratio of zinc to selenium may be at least 4:1 or 12:1.
The concentration of the metals may be at least 36mg/ml.
The trace element solution may comprise the following concentrations:
(a) at least 24 mg/ml zinc;
(b) at least 4 mg/ml manganese;
(c) at least 2 mg/ml selenium;
(d) at least 6 mg/ml copper; and
(e) at least 0.6 mg/ml Vitamin B12.
The concentration of the metals may be at least 90 mg/ml.
The solution may comprise chromium and/or iodine.
The solution may comprise butaphosphan to stabilize the Vitamin B12.
The inclusion of butaphosphan may enable the Vitamin B12 to remain more stable.
The inclusion of butaphosphan may have synergistic activity with the minerals.
The solution may be an injectable trace element solution.
The solution may be visually stable.
The invention also extends to a method of preparing a trace element solution as described herein.

DESCRIPTION OF EXAMPLE

Figure 1:
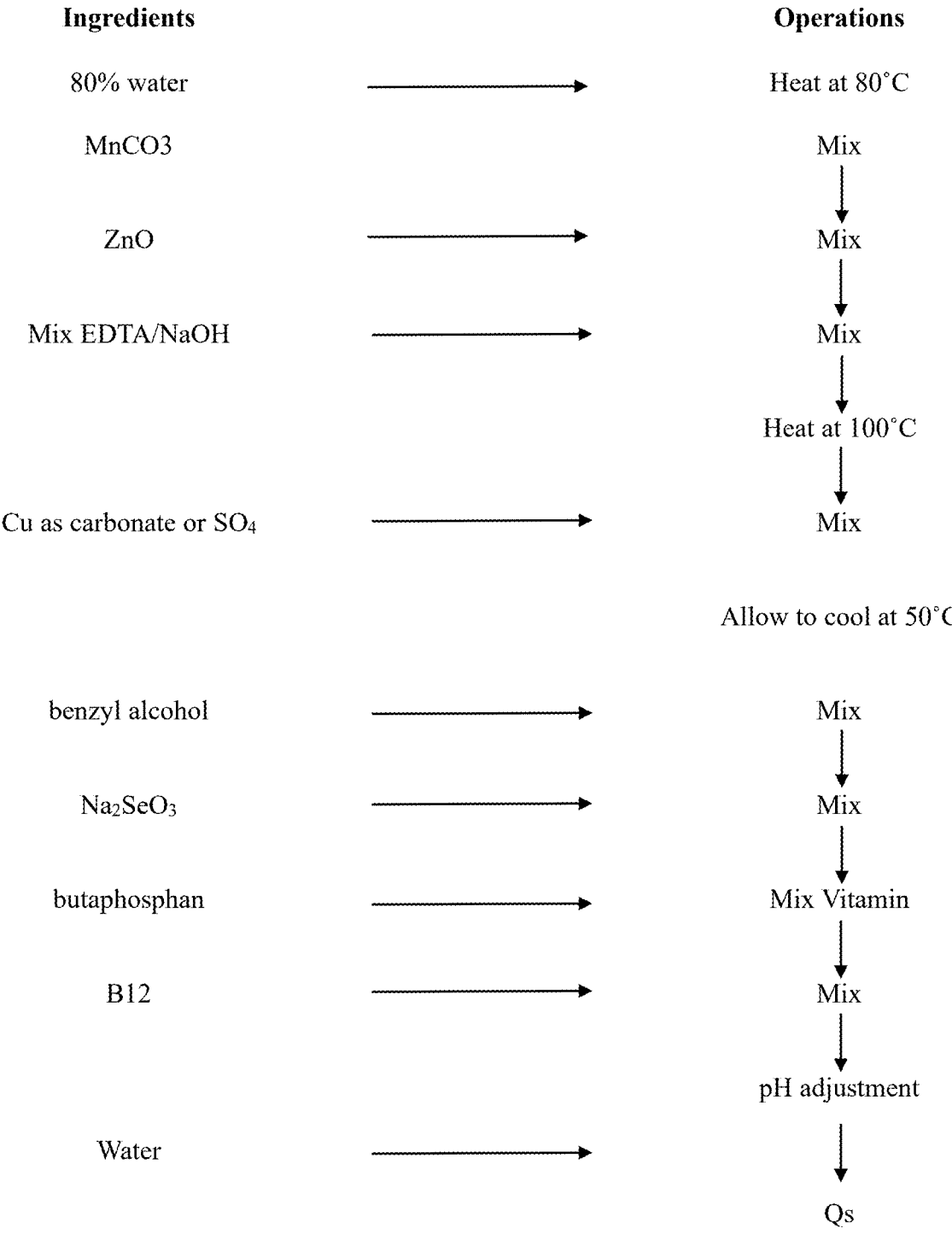
FIG. 1: Illustration of the process for preparing the solution of Formula 1.
Figure 2:
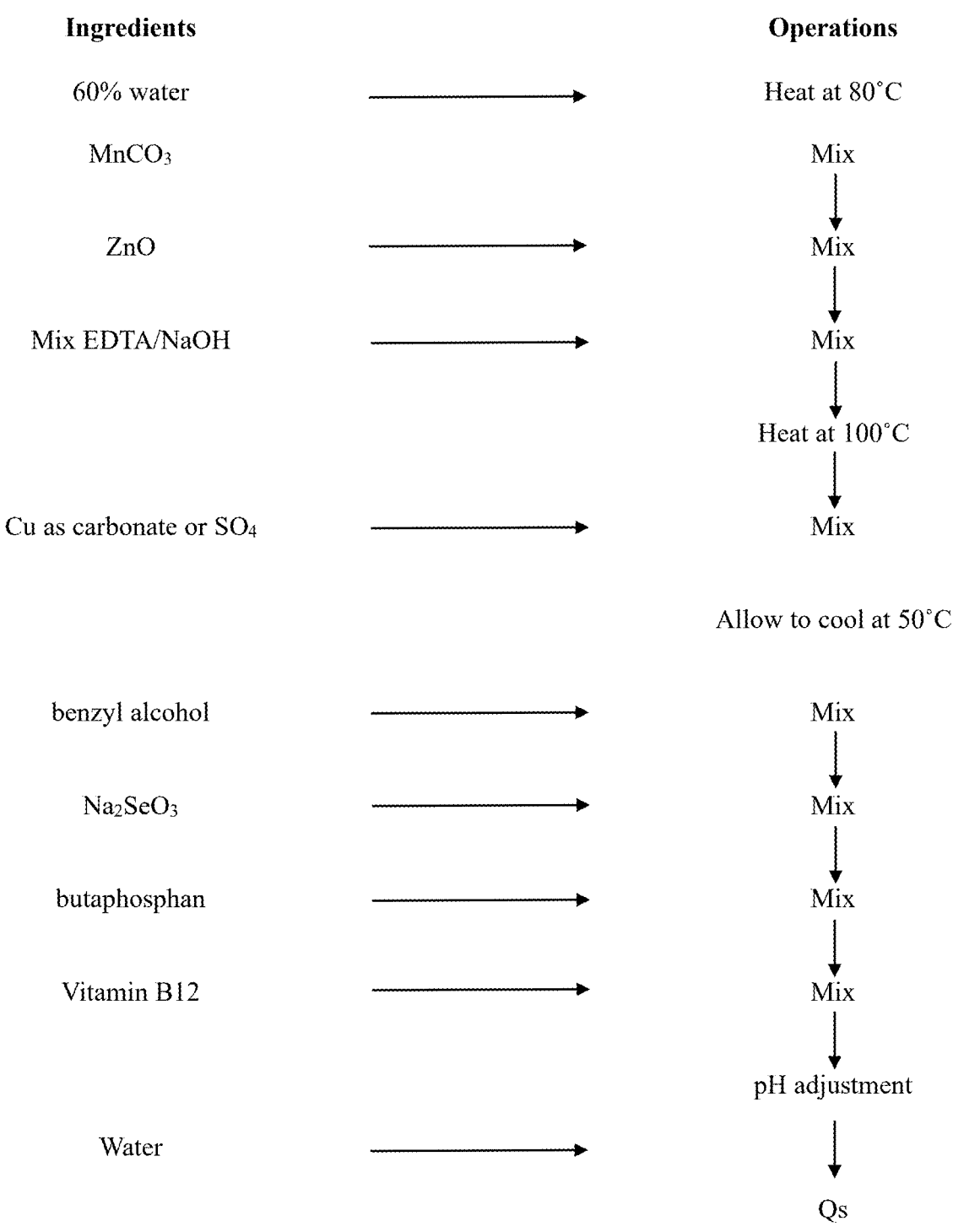
FIG. 2: Illustration of the process for preparing the solution of Formula 2.

The invention will now be described by way of an example of a trace element solution in accordance with the invention.

The example relates to a trace element solution predominantly to be used for cattle and includes the mineral elements zinc, manganese, selenium and copper and Vitamin B12.

According to the invention, a trace element solution, comprises the following metals:

(a) zinc;
(b) manganese;
(c) selenium; and
(d) copper;
and comprises Vitamin B12.

The ratio of zinc to manganese can be at least 2:1.

The ratio of zinc to manganese can be at least 4:1.

The ratio of zinc to copper can be at least 2:1 or 4:1.

The ratio of zinc to selenium can be at least 4:1 or 12:1.

As an example the concentration of the metals is at least 36 mg/ml.

As an example the trace element solution comprises the following concentrations:

(a) at least 24 mg/ml zinc;
(b) at least 4 mg/ml manganese;
(c) at least 2 mg/ml selenium;
(d) at least 6 mg/ml copper; and
(e) at least 0.6 mg/ml Vitamin B12.

In a further example, the concentration of the metals can be at least 90 mg/ml.

The solution can comprise chromium and/or iodine.

The solution comprises butaphosphan to stabilize the Vitamin B12.

The inclusion of butaphosphan may have synergistic activity with the minerals

The solution is generally an injectable trace element solution.

The solution is visually stable.

1. Objective of the study

The objective of the study is to develop a new formulation of an injectable trace element solution supplemented with Vitamin B12.

The new formulation is required to include the following characteristics:

(a) Active ingredients: Cu (6 mg/ml), Mn (4 mg/ml), Zn (24 mg/ml) and Se (2 mg/ml), Vitamin B12 (0.6 mg/ml) (A further example of the invention is to obtain a product with the following formulation: Active ingredients: Cu (15 mg/ml), Mn (10 mg/ml), Zn (60 mg/ml) and Se (5 mg/ml), Vitamin B12 (1.5 mg/ml))
(b) Application: Mineral and vitamin supplement 2. Formulation Plan The formulation plan consisted of performing two consecutive phases with the aim to select at the end one of several formulation candidates.

First phase consisted of feasibility formulation study:

Based on known injectable processes, with organometallics complex with EDTA, incorporation of vitamin B12 was screened by testing 3 possible different stabilizers.

Second Phase consists in evaluating the physical and chemical stability of the formulations which have been developed during precedent phase with the aim to select stable formulation prototypes.

Physical stability study was performed at 5° C., 25° C./60% RH and 40° C./75% RH: T0, T1, T2 and T3 months. A visual inspection was checked at different periods in order to control the absence of precipitation in the formulations.

Assay of vitamin B12 was followed up on stability at 25° C./60% RH and 40° C./75% RH: T0, T3 and T6 months.

3. Formulation Studies 3.1. Phase 1: Feasibility study

Based on known injectable processes, salts of zinc, copper and manganese were dissolved in water and complexed with EDTA, and then salt of selenium is added.

Incorporation of vitamin B12 with different stabilizers was screened.

Vitamin B12 is a water-soluble vitamin available as a dietary supplement. Vitamin B12 exists in several forms. Vitamin B12 cyanocobalamin is used for this study.

A vitamin B12 conforming to EP monograph was screened and received.

It is generally known that vitamins, and especially vitamin B12, are not very stable in solution and degradation is observed on storage.

According bibliographic researches and trials, the following stabilizers have been tested:

(a) Butaphosphan
(b) Glycine
(c) Antioxidants

Butaphosphan (according patent application US2011/0065665A1)

Butaphosphan is a phosphonic derivative acid.

Butanol described in US2011/0065665A1 has been replaced by use of benzyl alcohol (1%).

Note: butaphosphan is used with vitamin B12 in Catosal® formulation, from Bayer, and alone in Calphone® formulation, from Bayer.

Synonyms: Butaphosphan; (1-Butylamino-1-methyl-ethyl)-phosphinic acid

Molecular Formula: $C_7H_{18}NO_2P$

Formula Weight: 179.20

CAS Registry Number: 17316-67-5

In US2011/0065665A1: 10% of butaphosphan, 0.005% of vitamin B12, 3.0% of n-butanol/100% water Catosal® formulation: butaphosphan (100 mg), vitamin B12 (50 μg), n-butanol (30 mg)/1 ml Calphone®: formulation: butaphosphan (2 g)/500 ml The following concentrations of butaphosphan have been tested:

−5% w/v: a dark clear solution without particles is obtained

−10% w/v: a dark clear solution without particles is obtained

−20% w/v: incomplete solubilisation of butaphosphan

Then a quantity of stock solution of vitamin B12 was incorporated in the mix to have a final concentration of 0.15% w/v.

Physical stability study was performed on 5 and 10% w/v butaphosphan (with vitamin B12) solutions at ambient temperature:

T1 week: dark clear solution

T2 weeks: dark clear solution

T4 weeks: dark clear solution

Glycine

Glycine is an aminoacid.

Glycine is used with vitamin B12 and selenium mineral in Biodyl® formula, from Merial. Biodyl® formulation: glycine (5.0 g), vitamin B12 (0.050 g), selenium (0.045 g)/100 ml Glycine has been tried during development: 0.01% to 1% w/v.

Glycine conforming to EP monograph has been tested.

Following concentrations of glycine have been tested:

−5% w/v: a dark clear solution with particle is obtained

−10% w/v: a dark clear solution without particle is obtained

−15% w/v: a dark clear solution without particle is obtained

Physical stability study is performed on 5 and 15% w/v glycine (with vitamin B12) solutions at ambient temperature:

T1 week: dark clear solution with particle

T2 weeks: dark clear solution with particle

T4 weeks: dark clear solution with particle

Use of antioxidants

Use of antioxidant is evaluated, with butylhydroxyanisole BHA and butylhydroxytoluene BHT.

Other antioxidants have used: propyl gallate, ascorbic acid, rongalite, sodium metabisulphate.

Following antioxidant trials have been tested:

−1% w/v BHA and BHT: incomplete solubilisation

As a result of low solubility of BHA and BHT in water, process solubilisation of antioxidant(s) must be reviewed.

Conclusion

In conclusion, satisfactory results with butaphosphan solutions were obtained with different concentrations.

Results after 4 weeks of physical stability study showed dark clear solution.

These formulations were selected to go to next phase.

3.2. Phase 2: Laboratory batches

According results obtained with vitamin B12 and butaphosphan solutions, laboratory batches are performed.

| (a) Formula 1 | |
| --- | --- |
| Ingredients | Quantity per formula in mg |
| Manganese (Manganese carbonate) | 10.0 |
| Zinc (Zinc Oxide) | 60.0 |
| Copper (Copper Sulphate Pentahydrate) | 15.0 |
| Selenite (Sodium Selenite Anhydrous) | 5.0 |
| Butaphosphan | 100.0 |
| Vitamin B12 | 1.5 |

Excipients benzyl alcohol, edetic acid, sodium hydroxide and water for injection

| (b) Formula 2 | |
| --- | --- |
| Ingredients | Quantity per formula in mg |
| Manganese (Manganese Carbonate) | 4.0 |
| Zinc (Zinc Oxide) | 24.0 |
| Copper (Copper Sulphate Pentahydrate) | 6.0 |
| Selenite (Sodium Selenite Anhydrous) | 2.0 |
| Butaphosphan | 100.0 |
| Vitamin B12 | 1.5 |

Excipients benzyl alcohol, edetic acid, sodium hydroxide and water for injection 4. Phase 2: Stability studies A stability study at 25° C./60% RH and 40° C./75% RH was performed on formulations candidate during 3 months.

The aim of this study was to screen the formulations stable under ambient and accelerated conditions.

A visual inspection checked at different periods in order to control the absence of precipitation in the formulations: at 5° C., 25° C./60% RH and 40° C./75% RH: T0, T1, T2 and T3 months.

Assays of Vitamin B12 were evaluated: follow up on stability at 25° C./60% RH and 40° C./75% RH: T0, T3 and T6 months.

6

Summary

The method of preparing a trace element solution in accordance with the invention thus enables the production of an injectable solution comprising an adequate trace mineral concentration and Vitamin B12 so that a 5 to 10 millilitre injection can make a significant impact on the trace mineral status of the animal and an injection is provided at a rate of between 1 ml per 50 kg bodyweight (BW) and 1 ml per 100 kg BW, i.e. a practically applicable injectable supplement and a product that can improve the trace mineral status of an animal is provided. This is important as livestock producers will only inject livestock if a real benefit can be demonstrated. The subcutaneous injection is the preferred route to minimize tissue damage, but intra-muscular injection can also be used.

The invention claimed is:

1. An injectable trace element solution, the solution comprising at least the following metals:

(a) 24 mg/ml zinc;

(b) 4 mg/ml manganese;

(c) 2 mg/ml selenium;

(d) 6 mg/ml copper;

at least 0.6 mg/ml Vitamin B12; and butaphosphan, wherein precipitation is visually absent in the injectable trace element solution exposed at 25° C. and 60% relative humidity for 3 months.

2. The injectable trace element solution of claim 1, wherein the zinc is derived from zinc oxide.

3. The injectable trace element solution of claim 1, wherein the copper is derived from copper carbonate or copper sulphate pentahydrate.

4. The injectable trace element solution of claim 1, wherein the selenium is derived from sodium selenite anhydrous.

5. The injectable trace element solution of claim 1, wherein:

the manganese is derived from manganese carbonate;

the zinc is derived from zinc oxide;

the copper is derived from copper carbonate or copper sulphate pentahydrate, and the selenium is derived from sodium selenite anhydrous.

6. The injectable trace element solution of claim 1 further comprising benzyl alcohol.

7. The injectable trace element solution of claim 1 further comprising chromium.

8. The injectable trace element colution of claim 1 further comprising iodine.

9. An injectable trace element solution, the solution comprising at least the following metals:

(a) 24 mg/ml zinc;

(b) 4 mg/ml manganese;

(c) 2 mg/ml selenium;

(d) 6 mg/ml copper;

at least 0.6 mg/ml Vitamin B12; and butaphosphan, wherein the Vitamin B12 is chemically stable in the injectable trace element solution exposed at 25° C. and 60% relative humidity for 3 months.

10. The injectable trace element solution of claim 9, wherein the Vitamin B12 is chemically stable in the injectable trace element solution exposed at 25° C. and 60% relative humidity for 6 months.

11. The injectable trace element solution of claim 9, wherein precipitation is visually absent in the injectable trace element solution exposed at 25° C. and 60% relative humidity for 3 months.

12. The injectable trace element solution of claim 10, wherein precipitation is visually absent in the injectable trace element solution exposed at 25° C. and 60% relative humidity for 3 months.

* * * * *